United States Patent

Matsuda

(10) Patent No.: US 10,292,591 B2
(45) Date of Patent: May 21, 2019

(54) ELECTRONIC DEVICE FOR ADJUSTING POWER TO AN EARPHONE TRANSMITTER

(71) Applicant: KYOCERA CORPORATION, Kyoto (JP)

(72) Inventor: Munehito Matsuda, Oumihachiman (JP)

(73) Assignee: KYOCERA CORPORATION, Kyoto (JP)

(*) Notice: Subject to any disclaimer, the term of this patent is extended or adjusted under 35 U.S.C. 154(b) by 273 days.

(21) Appl. No.: 15/274,973

(22) Filed: Sep. 23, 2016

(65) Prior Publication Data

US 2017/0007131 A1 Jan. 12, 2017

Related U.S. Application Data

(63) Continuation of application No. PCT/JP2015/059438, filed on Mar. 26, 2015.

(30) Foreign Application Priority Data

Mar. 26, 2014 (JP) .................................. 2014-064135

(51) Int. Cl.
*A61B 5/00* (2006.01)
*A61B 5/024* (2006.01)
(52) U.S. Cl.
CPC ........ *A61B 5/0062* (2013.01); *A61B 5/02416* (2013.01); *A61B 5/6803* (2013.01); *A61B 5/6817* (2013.01); *A61B 2560/0209* (2013.01)
(58) Field of Classification Search
None
See application file for complete search history.

(56) References Cited

U.S. PATENT DOCUMENTS

| 9,560,994 | B2* | 2/2017 | McCutcheon | A61B 5/14551 |
| 9,622,685 | B2* | 4/2017 | Wisbey | G09B 19/0038 |
| 2004/0225207 | A1 | 11/2004 | Bae | |
| 2010/0113948 | A1* | 5/2010 | Yang | A61B 5/02416 600/500 |
| 2010/0262025 | A1* | 10/2010 | Hu | A61B 5/02416 600/504 |
| 2013/0137946 | A1* | 5/2013 | Geske | A61B 5/02433 600/324 |
| 2015/0100141 | A1* | 4/2015 | Hughes | A61B 5/1118 700/92 |
| 2015/0190078 | A1* | 7/2015 | Lisogurski | A61B 5/14551 600/324 |
| 2016/0192039 | A1* | 6/2016 | Negi | H04M 1/72569 340/870.07 |

FOREIGN PATENT DOCUMENTS

JP 2007-054650 A 3/2007

* cited by examiner

*Primary Examiner* — Brian T Gedeon
(74) *Attorney, Agent, or Firm* — Duane Morris LLP

(57) ABSTRACT

At least one processor is configured to control transmission of infrared rays from an infrared transmitter. A signal reception unit is configured to receive waveform signals of the infrared rays received by an infrared receiver. The at least one processor is configured to measure pulses of a user who wears an earphone based on the waveform signals and to control a transmission pattern of the infrared rays from the infrared transmitter based on which of accuracy in measurement of pulses and power saving is prioritized.

20 Claims, 18 Drawing Sheets

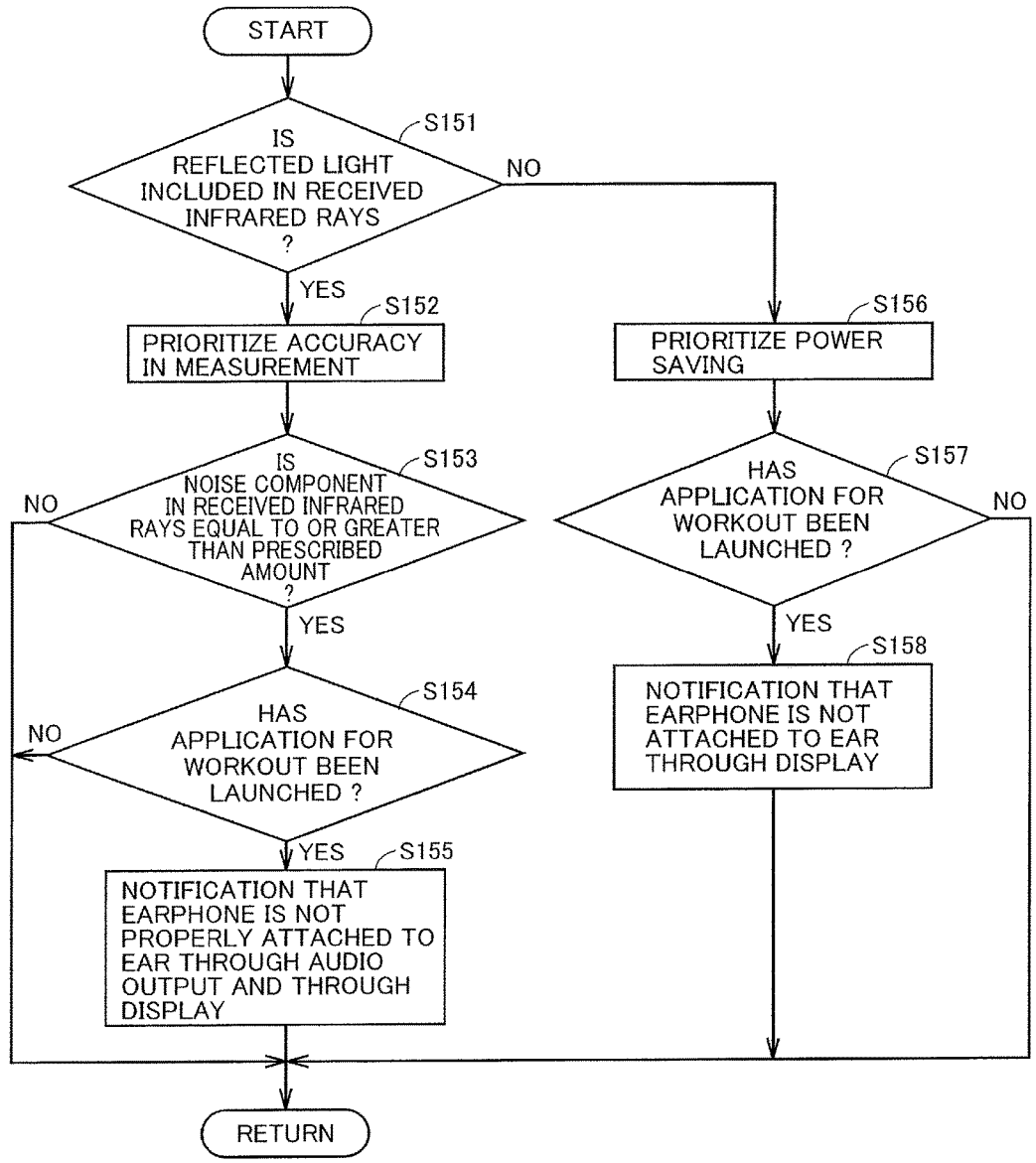

ELECTRONIC DEVICE FOR ADJUSTING POWER TO AN EARPHONE TRANSMITTER

CROSS-REFERENCE TO RELATED APPLICATION

The present application is a continuation based on PCT Application No. PCT/JP2015/059438 filed on Mar. 26, 2015, which claims the benefit of Japanese Application No. 2014-064135 filed on Mar. 26, 2014. PCT Application No. PCT/JP2015/059438 is entitled "Electronic Instrument," and Japanese Application No. 2014-064135 is entitled "Electronic Device." The contents of which are incorporated by reference herein in their entirety.

FIELD

The present disclosure relates to an electronic device and particularly to an electronic device which transmits electric power to another electronic device.

BACKGROUND

A device which emits light to an earhole portion of a user so as to measure pulses of the user based on reflected light has been known.

For example, a device in one example of the background art includes a PPG measurement module which detects light conveyed from the skin in the earhole and outputs a PPG signal containing biological information. The PPG measurement module includes a light source unit which emits light to the skin in the earhole and a light detection unit which detects light emitted from the light source unit and reflected by the skin in the earhole. A PPG signal processing unit includes a pulse detection unit which measures pulses by detecting a peak of a PPG signal and calculating a time interval between peaks.

SUMMARY

An electronic device in one embodiment controls an earphone which includes an infrared transmitter and an infrared receiver. The electronic device includes at least one processor configured to control transmission of infrared rays from the infrared transmitter and a reception unit configured to receive waveform signals of the infrared rays received by the infrared receiver. The at least one processor is configured to measure pulses of a user who wears the earphone based on the waveform signals and to control a transmission pattern of the infrared rays from the infrared transmitter based on which of accuracy in measurement of pulses and power saving is prioritized.

BRIEF DESCRIPTION OF THE DRAWINGS

FIG. 29 is a flowchart showing a procedure of processing for notification in a sixteenth embodiment.

DETAILED DESCRIPTION

Embodiments will be described below with reference to the drawings.

An amount of consumption of electric power increases when accuracy in measurement of pulses is enhanced, whereas accuracy in measurement of pulse lowers when an amount of consumption of electric power is decreased. With a conventional device, however, disadvantageously, switching between priority on accuracy in measurement of pulses and priority on power saving depending on a situation cannot be made. The problem can be solved by the disclosure below.

[First Embodiment]

Figure 1:
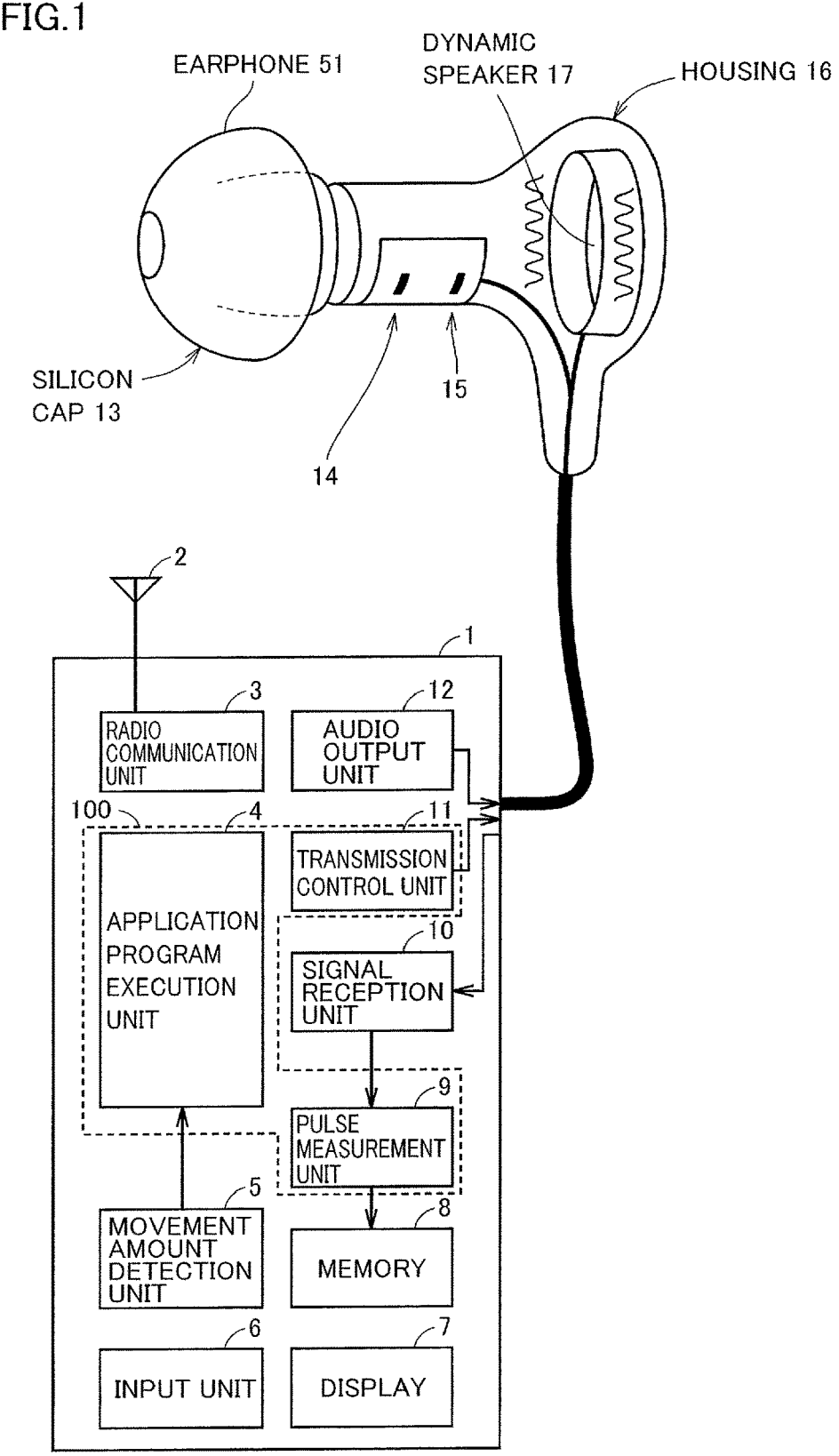
FIG. 1 is a diagram showing a configuration of a smartphone and an earphone connected to the smartphone in an embodiment.

FIG. 1 is a diagram showing a configuration of a smartphone 1 and an earphone 51 connected to smartphone 1 in an embodiment.

Referring to FIG. 1, smartphone 1 includes an antenna 2, a radio communication unit 3, a movement amount detection unit 5, an input unit 6, a display 7, a memory 8, an audio output unit 12, a signal reception unit 10, and at least one processor 100.

At least one processor 100 can provide control and processing capability to perform various functions of an application program execution unit 4, a transmission control unit 11, and a pulse measurement unit 9.

In accordance with various embodiments, the at least one processor 100 may be implemented as a single integrated circuit (IC) or as multiple communicatively coupled IC's and/or discrete circuits. It is appreciated that the at least one processor 100 can be implemented in accordance with various known technologies. In one embodiment, the processor 100 includes one or more circuits or units configurable to perform one or more data computing procedures or processes by executing instructions stored in an associated memory, for example. In other embodiments, the processor 100 may be implemented as firmware (e.g. discrete logic components) configured to perform one or more data computing procedures or processes. In accordance with various embodiments, the processor 100 may include one or more processors, controllers, microprocessors, microcontrollers, application specific integrated circuits (ASICs), digital signal processors, programmable logic devices, field programmable gate arrays, or any combination of these devices or structures, or other known devices and structures, to perform the functions described herein.

Earphone 51 includes a silicon cap 13, a housing 16, a dynamic speaker 17, an infrared transmitter 14, and an infrared receiver 15.

In various embodiments, input unit 6 may be implemented using any input technology or device known in the art such as, for example, a QWERTY keyboard, a pointing device (e.g., a mouse), a joy stick, a stylus, a touch screen display panel, a key pad, one or more buttons, etc., or any combination of these technologies.

Display 7 includes, for example, a liquid crystal display.

Radio communication unit 3 can establish radio communication with a radio base station through antenna 2.

Application program execution unit 4 can execute various applications such as a music application and an application for workout.

Movement amount detection unit 5 includes an acceleration sensor and can detect an amount of movement of smartphone 1.

Memory 8 can store a result of measurement of pulses and the like.

Audio output unit 12 can output voice and sound to the outside. Audio output unit 12 can output voice and sound to the outside through dynamic speaker 17 in earphone 51 while earphone 51 is connected to smartphone 1.

Transmission control unit 11 can control transmission of infrared rays from infrared transmitter 14.

Signal reception unit 10 can receive waveform signals of infrared rays received by infrared receiver 15.

Pulse measurement unit 9 can measure pulses of a user who wears earphone 51 based on waveform signals of received infrared rays.

Housing 16 can accommodate dynamic speaker 17, infrared transmitter 14, and infrared receiver 15. Housing 16 can function as a portion of sounding of voice and sound output from dynamic speaker 17. Silicon cap 13 can be attached to housing 16.

Infrared transmitter 14 can transmit infrared rays. Infrared receiver 15 can receive infrared rays.

Figure 2:
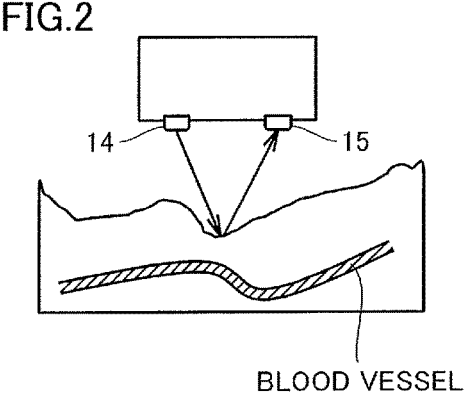
FIG. 2 is a diagram showing transmission and reception of infrared rays.

FIG. 2 is a diagram showing transmission and reception of infrared rays.

Earphone 51 can be attached to an ear of a user such that infrared transmitter 14 and infrared receiver 15 face the skin of an external ear.

Transmission waves transmitted from infrared transmitter 14 can be reflected by the skin of the external ear and received as reception waves by infrared receiver 15.

Figure 3:
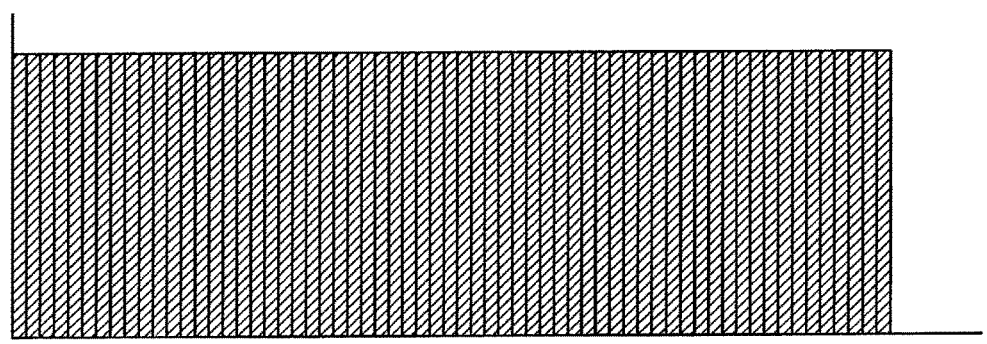
FIG. 3 is a diagram showing an example of transmission waveforms.
Figure 4:
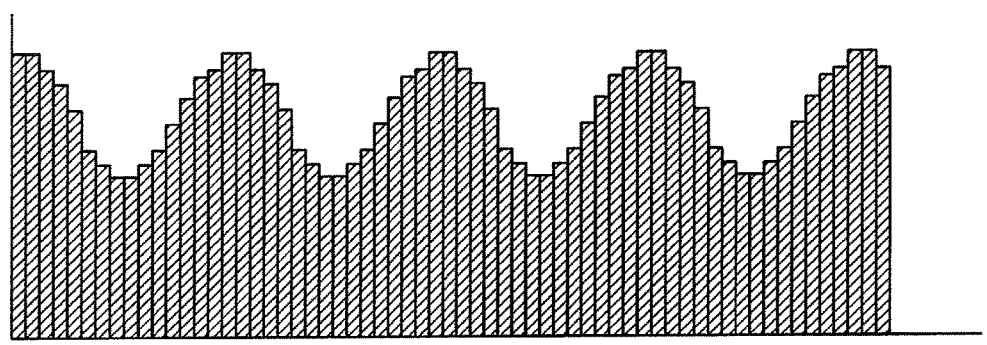
FIG. 4 is a diagram showing an example of reception waveforms.

Blood vessels are located under the skin of the external ear and blood flows through the blood vessels. For example, when infrared transmitter 14 transmits emission waves as in FIG. 3, signal waveforms of reception waves received by infrared receiver 15 are as shown in FIG. 4. As the blood vessels contract with pulses, an amount of absorption of infrared rays is varied and a period of reception waves is in synchronization with a period of pulses. Pulses can be calculated based on the period of the reception waves.

Figure 5:
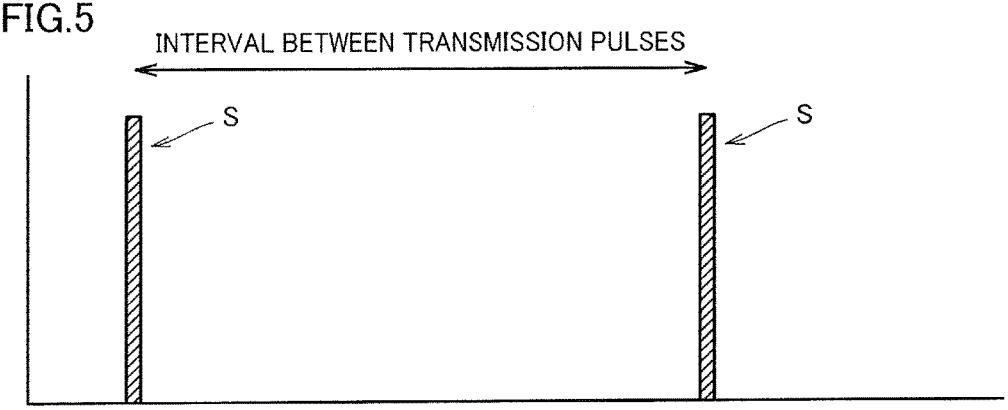
FIG. 5 shows an example of transmission pulses of infrared rays output from an infrared transmitter.

FIG. 5 shows an example of transmission pulses S of infrared rays output from infrared transmitter 14.

Figure 6:
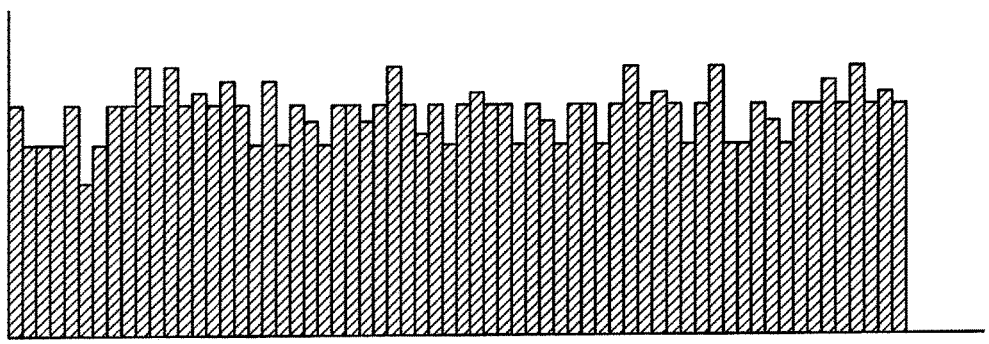
FIG. 6 is a diagram showing one example of reception waves received by an infrared receiver when transmission pulses S in FIG. 5 are transmitted.

FIG. 6 is a diagram showing one example of reception waves received by infrared receiver 15 when transmission pulses S in FIG. 5 are transmitted. This example represents a user not wearing earphone 51 in the ear. When the user is not wearing earphone 51 in the ear, reception waves consist of noise components originating from external light (for example, solar rays or infrared rays output from a fluorescent lamp).

Figure 7:
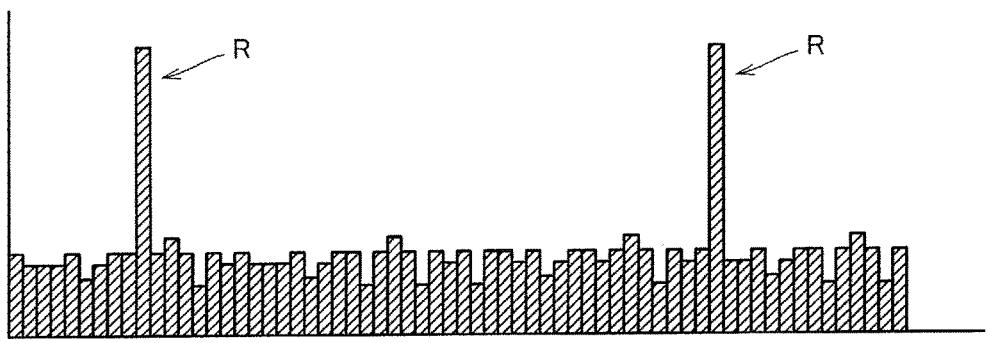
FIG. 7 is a diagram showing another example of reception waves received by the infrared receiver when transmission pulses S in FIG. 5 are transmitted.

FIG. 7 shows another example of reception waves received by infrared receiver 15 when transmission pulses in FIG. 5 are transmitted. This example represents a user wearing earphone 51 in the ear. When the user is wearing earphone 51 in the ear, reception waves include reflection pulses R resulting from reflection of transmission pulses S in FIG. 5 at the skin of the external ear of the user.

Figure 8:
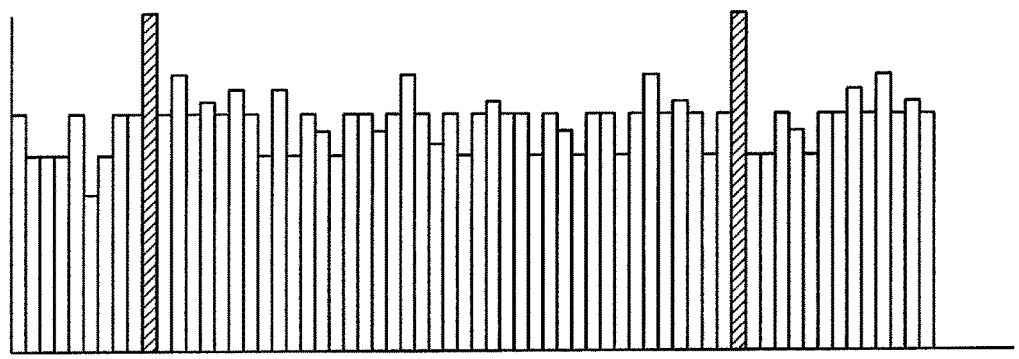
FIG. 8 is a diagram showing yet another example of reception waves received by the infrared receiver when transmission pulses S in FIG. 5 are transmitted.

FIG. 8 is a diagram showing yet another example of reception waves received by infrared receiver 15 when transmission pulses in FIG. 5 are transmitted.

When earphone 51 is not properly accommodated in the ear, the reception waves include reflected waves and external light. In this case, measurement of pulses is enabled by increasing a ratio of components of reflection waves included in the reception waves by increasing transmission power of infrared rays as will be described later.

Figure 9:
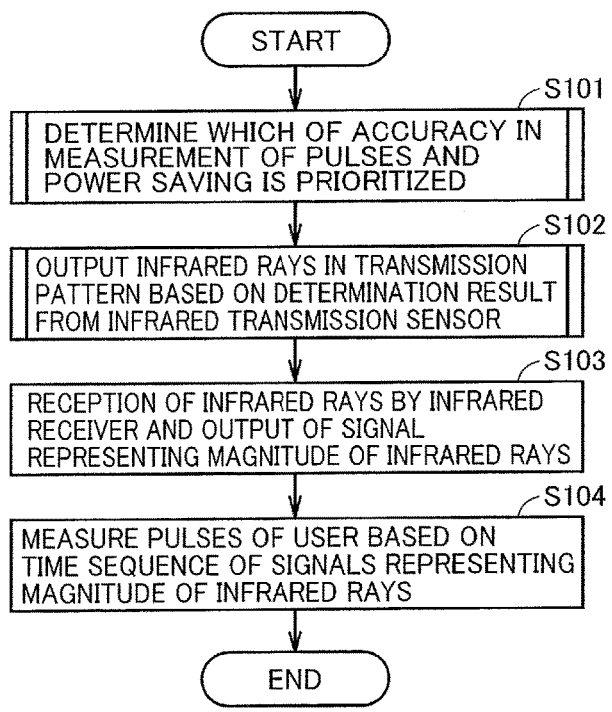
FIG. 9 is a flowchart showing a procedure of measurement of pulses in a first embodiment.

FIG. 9 is a flowchart showing a procedure of measurement of pulses in a first embodiment.

In step S101, transmission control unit 11 can determine which of accuracy in measurement of pulses and power saving is prioritized.

In step S102, transmission control unit 11 can control transmission such that infrared rays in a transmission pattern based on a result of determination are transmitted from infrared transmitter 14.

In step S103, infrared receiver 15 can receive infrared rays and output waveform signals of the received infrared rays.

In step S104, signal reception unit 10 can receive waveform signals of the infrared rays from infrared receiver 15. Pulse measurement unit 9 can measure pulses of a user based on the waveform signals of the received infrared rays.

Figure 10:
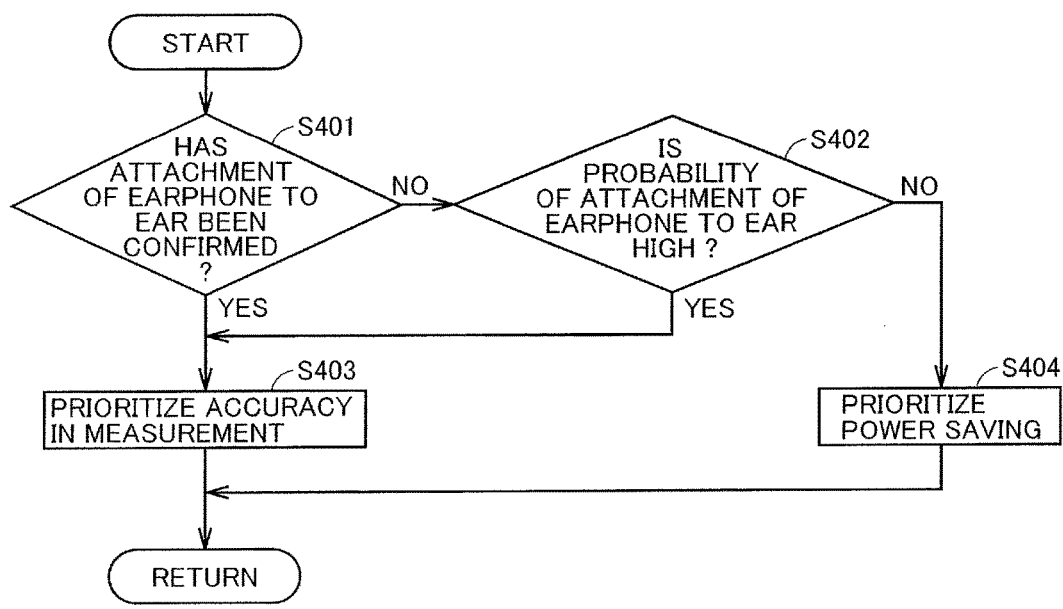
FIG. 10 is a flowchart showing the first embodiment of determination of prioritized contents in step S101 in FIG. 9.

FIG. 10 is a flowchart showing the first embodiment of determination of prioritized contents in step S101 in FIG. 9.

When attachment of earphone 51 to an ear of a user is confirmed in step S401 (S401: YES), the process proceeds to step S403. When attachment of earphone 51 to the ear of the user is not confirmed (S401: NO), the process proceeds to step S402. When probability of attachment of earphone 51 to the ear of the user is determined as relatively high in step S402 (S402: YES), the process proceeds to step S403. When probability of attachment of earphone 51 to the ear of the user is determined as relatively low (S402: NO), the process proceeds to step S404.

In step S403, transmission control unit 11 can prioritize accuracy in measurement.

In step S404, transmission control unit 11 can prioritize power saving. It is useless to frequently send infrared rays during a period in which earphone 51 is not inserted in the ear, and a consumed current during a period in which earphone 51 is not inserted in the ear can significantly be reduced by sending pulse signals at some interval.

Figure 11:
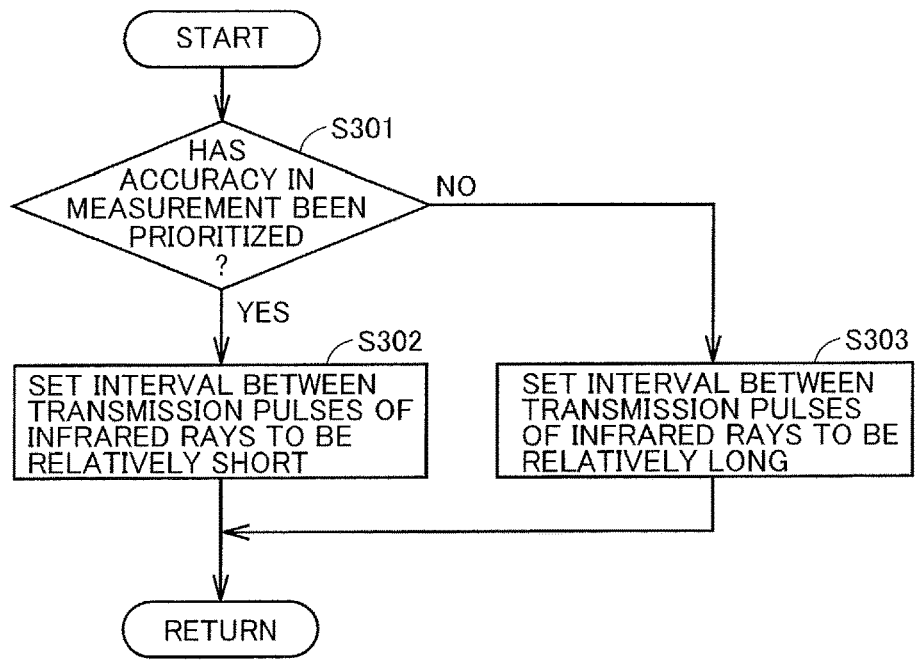
FIG. 11 is a flowchart showing the first embodiment of control of a transmission pattern in step S102 in FIG. 9.

FIG. 11 is a flowchart showing the first embodiment of control of a transmission pattern in step S102 in FIG. 9.

When accuracy in measurement has been prioritized in step S301 (S301: YES), the process proceeds to step S302. When power saving has been prioritized (S301: NO), the process proceeds to step S303.

In step S302, transmission control unit 11 can set an interval between transmission pulses of infrared rays from infrared transmitter 14 to be relatively short. For example, transmission control unit 11 can set an interval between transmission pulses to d1.

In step S303, transmission control unit 11 can set an interval between transmission pulses of infrared rays from infrared transmitter 14 to be relatively long. For example, transmission control unit 11 can set an interval between transmission pulses to d2. Here, relation of d1<d2 is satisfied. Values for d1 and d2 may be designated by a user through input unit 6.

As set forth above, in the first embodiment, when attachment of earphone 51 to an ear is confirmed or when probability of attachment is high although attachment has not been confirmed, accuracy in measurement is prioritized and an interval between transmission pulses is made shorter. Therefore, pulses of a user can be measured with high accuracy. When attachment of earphone 51 to an ear is not confirmed and probability of attachment is low, power saving is prioritized and an interval between transmission pulses is made longer. Therefore, consumption of high electric power in spite of high probability of unsuccessful measurement can be prevented.

[Second Embodiment]

In a second embodiment, when infrared rays received by infrared receiver 15 include reflected light of infrared rays transmitted from infrared transmitter 14, transmission control unit 11 can prioritize accuracy in measurement, assuming that attachment of earphone 51 to an ear of a user has been confirmed.

Figure 12:
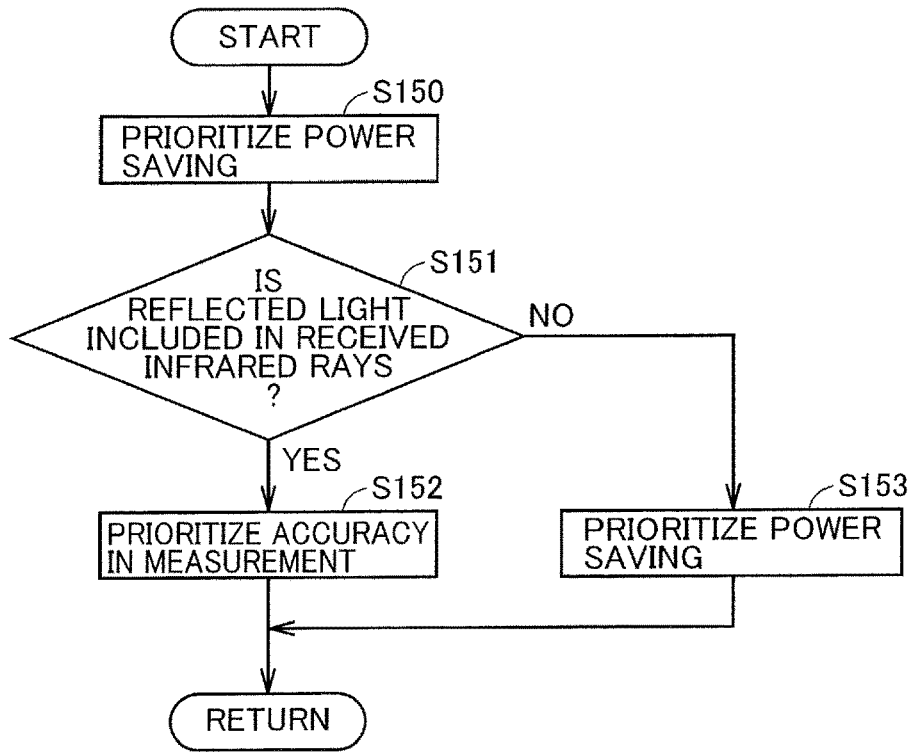
FIG. 12 is a flowchart showing a second embodiment of determination of prioritized contents in step S101 in FIG. 9.

FIG. 12 is a flowchart showing the second embodiment of determination of prioritized contents in step S101 in FIG. 9.

In step S150, transmission control unit 11 can prioritize power saving. This is because infrared rays are transmitted for determining whether or not received infrared rays include reflected light and accuracy in measurement is not required.

When received infrared rays include reflected light of infrared rays transmitted from infrared transmitter 14 in step S151 (S151: YES), the process proceeds to step S152. When the received infrared rays do not include reflected light (S151: NO), the process proceeds to step S153.

In step S152, transmission control unit 11 can prioritize accuracy in measurement.

In step S153, transmission control unit 11 can prioritize power saving.

[Third Embodiment]

In a third embodiment, transmission control unit 11 can prioritize accuracy in measurement because it is highly likely that a user wears earphone 51 in an ear for measurement of pulses at the timing immediately after connection between earphone 51 and smartphone 1.

Figure 13:
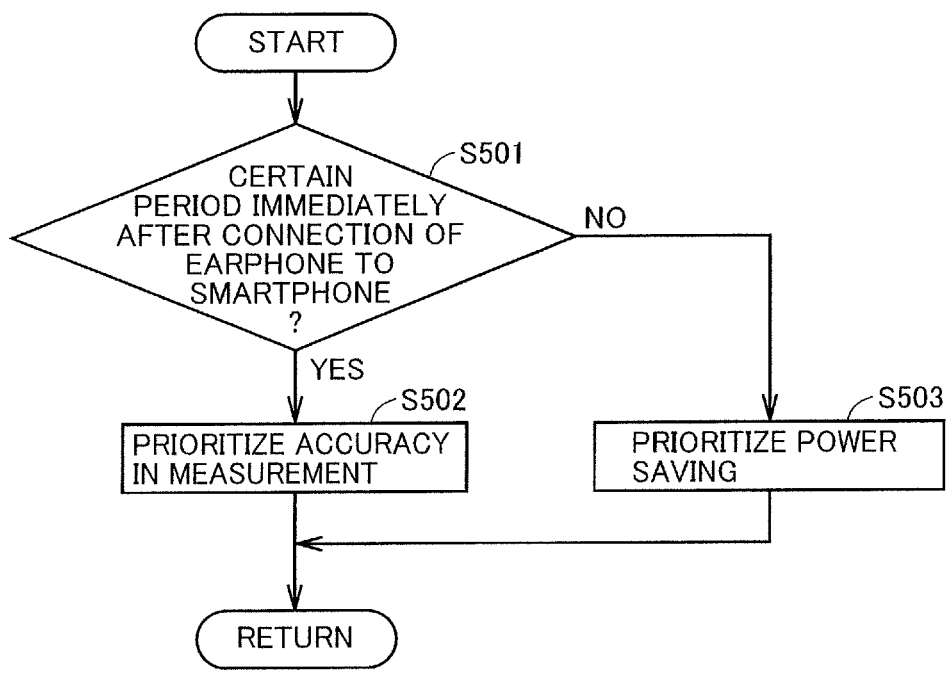
FIG. 13 is a flowchart showing a third embodiment of determination of prioritized contents in step S101 in FIG. 9.

FIG. 13 is a flowchart showing the third embodiment of determination of prioritized contents in step S101 in FIG. 9.

When the current time point is included in a certain period immediately after connection of earphone 51 to smartphone 1 in step S501 (S501: YES), the process proceeds to step S502. When the current time point is not included in the certain period (S501: NO), the process proceeds to step S503.

In step S502, transmission control unit 11 can prioritize accuracy in measurement.

In step S503, transmission control unit 11 can prioritize power saving.

[Fourth Embodiment]

In a fourth embodiment, when attachment of earphone 51 to an ear is not confirmed even after lapse of a certain period (for example, 1 minute) since connection between earphone 51 and smartphone 1, transmission control unit 11 can determine that a user is less likely to attach earphone 51 to an ear for measurement of pulses also after that timing and can prioritize power saving.

Figure 14:
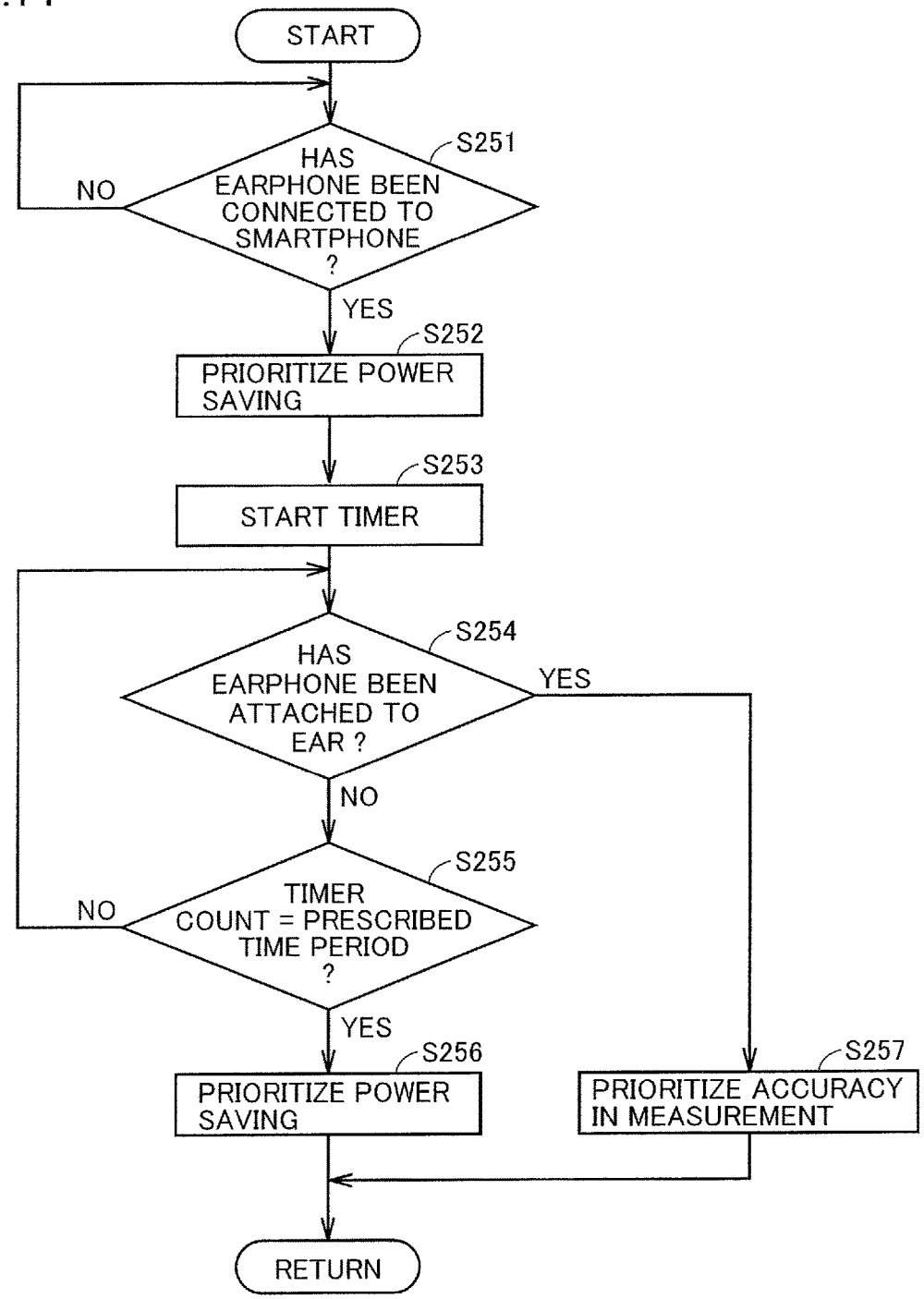
FIG. 14 is a flowchart showing a fourth embodiment of determination of prioritized contents in step S101 in FIG. 9.

FIG. 14 is a flowchart showing the fourth embodiment of determination of prioritized contents in step S101 in FIG. 9.

When earphone 51 has been connected to smartphone 1 in step S251 (S251: YES), the process proceeds to step S252.

In step S252, transmission control unit 11 can prioritize power saving. This is because infrared rays are transmitted for determining whether or not received infrared rays include reflected light and accuracy in measurement is not required.

In step S253, transmission control unit 11 can start a timer.

When attachment of earphone 51 to an ear has been confirmed in step S254 (S254: YES), the process proceeds to step S257. When attachment of earphone 51 to an ear has not been confirmed (S254: NO), the process proceeds to step S255.

When a timer count reaches a prescribed time period in step S255 (S255: YES), the process proceeds to step S256. When a timer count has not reached the prescribed time period (S255: NO), the process returns to step S254.

In step S256, transmission control unit 11 can prioritize power saving. In step S257, transmission control unit 11 can prioritize accuracy in measurement.

[Fifth Embodiment]

In a fifth embodiment, at the timing of launch of a music application or an application for workout (an exercise program) in smartphone 1, a user is highly likely to wear earphone 51 in the ear. Therefore, transmission control unit 11 can prioritize accuracy in measurement.

Figure 15:
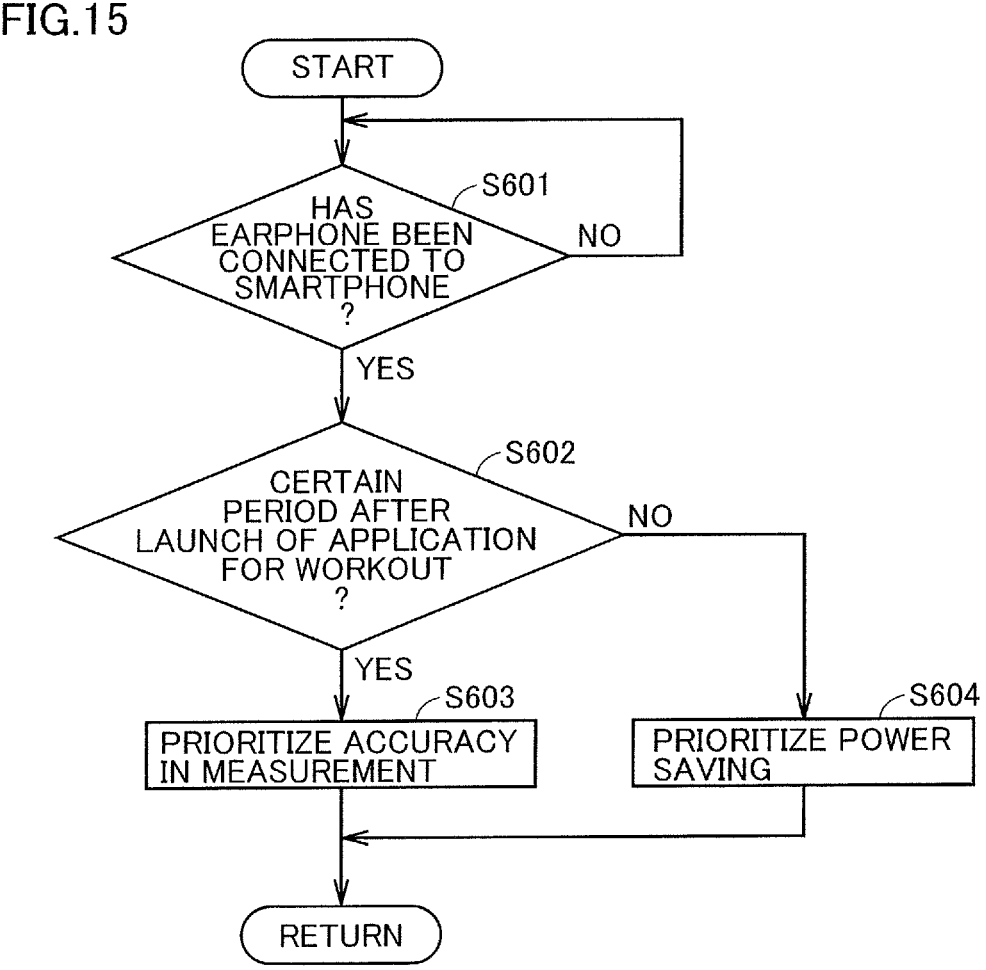
FIG. 15 is a flowchart showing a fifth embodiment of determination of prioritized contents in step S101 in FIG. 9.

FIG. 15 is a flowchart showing the fifth embodiment of determination of prioritized contents in step S101 in FIG. 9.

When earphone 51 has been connected to smartphone 1 in step S601 (S601: YES), the process proceeds to step S602.

When the current time point is included in a certain period after launch of an application for workout in step S602 (S602: YES), the process proceeds to step S603. When the current time point is not included in the certain period (S602: NO), the process proceeds to step S604.

In step S603, transmission control unit 11 can prioritize accuracy in measurement.

In step S604, transmission control unit 11 can prioritize power saving.

[Sixth Embodiment]

In a sixth embodiment, transmission control unit 11 addresses a user who measures pulses during workout. When movement is not detected in smartphone 1 used by the user, it is highly likely that the user is not doing workout and the user is not wearing earphone 51 in the ear. Therefore, power saving can be prioritized.

Figure 16:
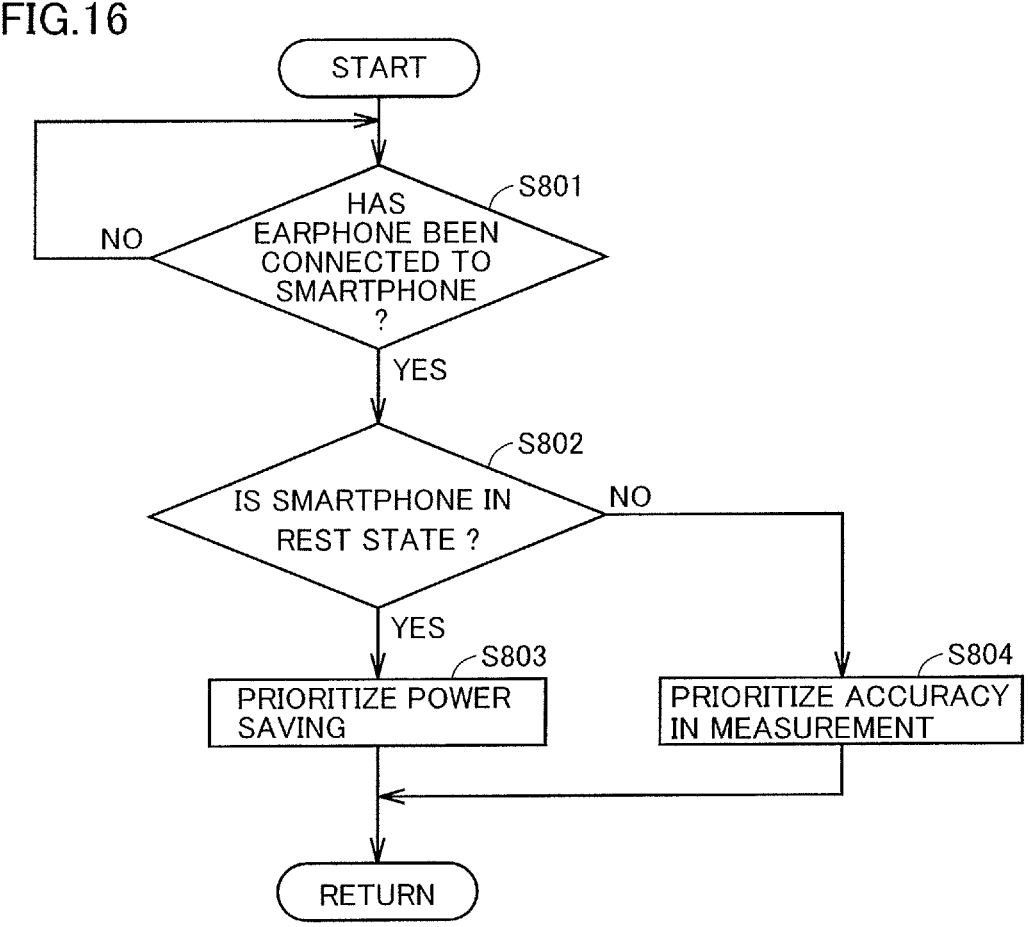
FIG. 16 is a flowchart showing a sixth embodiment of determination of prioritized contents in step S101 in FIG. 9.

FIG. 16 is a flowchart showing the sixth embodiment of determination of prioritized contents in step S101 in FIG. 9.

When earphone 51 has been connected to smartphone 1 in step S801 (S801: YES), the process proceeds to step S802.

When movement amount detection unit 5 detects a rest state of smartphone 1 in step S802 (S802: YES), the process proceeds to step S803. When movement amount detection unit 5 detects movement of smartphone 1 (S802: NO), the process proceeds to step S804.

In step S803, transmission control unit 11 can prioritize power saving.

In step S804, transmission control unit 11 can prioritize accuracy in measurement.

[Seventh Embodiment]

In a seventh embodiment, smartphone 1 can switch between a normal mode and a power saving mode which is an operation mode in which the smartphone operates with power consumption lower than in the normal mode. In the seventh embodiment, when smartphone 1 is set to the power saving mode, transmission control unit 11 can prioritize power saving.

Figure 17:
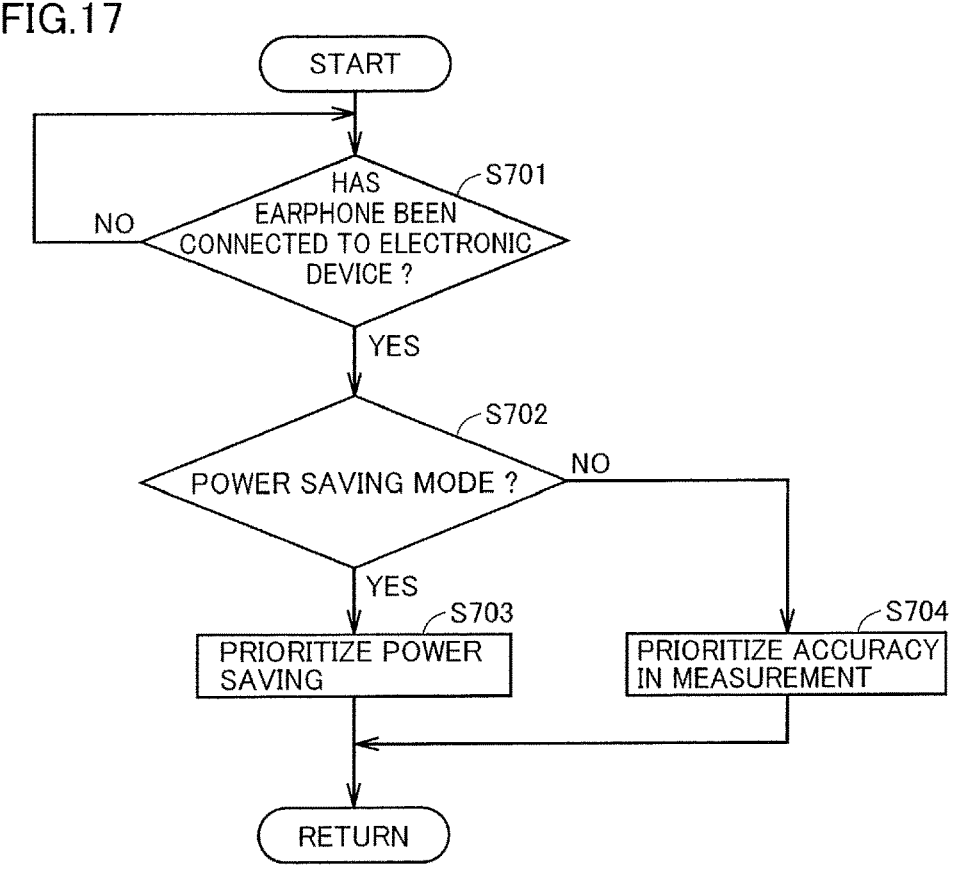
FIG. 17 is a flowchart showing a seventh embodiment of determination of prioritized contents in step S101 in FIG. 9.

FIG. 17 is a flowchart showing the seventh embodiment of determination of prioritized contents in step S101 in FIG. 9.

When earphone 51 has been connected to smartphone 1 in step S701 (S701: YES), the process proceeds to step S702.

When the power saving mode has been set in step S702 (S702: YES), the process proceeds to step S703. When the power saving mode has not been set (S702: NO), the process proceeds to step S704.

In step S703, transmission control unit 11 can prioritize power saving.

In step S704, transmission control unit 11 can prioritize accuracy in measurement.

When the power saving mode is on, not only power saving may be prioritized but also the certain period in the third embodiment may be made shorter.

[Eighth Embodiment]

In an eighth embodiment, when measured pulses are expected to be fast, transmission control unit 11 can prioritize accuracy in measurement. For example, by prioritizing accuracy in measurement and making an interval between infrared rays shorter, an interval between timings of reception of reflected light is also shorter and measurement of fast pulses is allowed.

Figure 18:
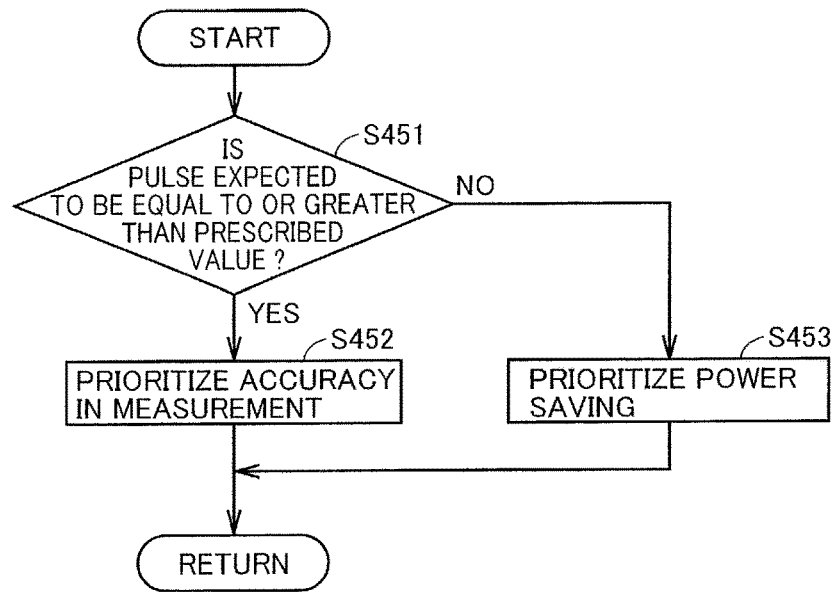
FIG. 18 is a flowchart showing an eighth embodiment of determination of prioritized contents in step S101 in FIG. 9.

FIG. 18 is a flowchart showing the eighth embodiment of determination of prioritized contents in step S101 in FIG. 9.

When pulses measured by pulse measurement unit 9 are expected to be equal to or greater than a prescribed value in step S451 (S451: YES), the process proceeds to step S452. When pulses measured by pulse measurement unit 9 are expected to be smaller than the prescribed value (S451: NO), the process proceeds to step S453.

In step S452, transmission control unit 11 can prioritize accuracy in measurement.

In step S453, transmission control unit 11 can prioritize power saving.

[Ninth Embodiment]

In a ninth embodiment, when the user is doing workout such as running and pulses are expected to be fast, transmission control unit 11 can prioritize accuracy in measurement.

Figure 19:
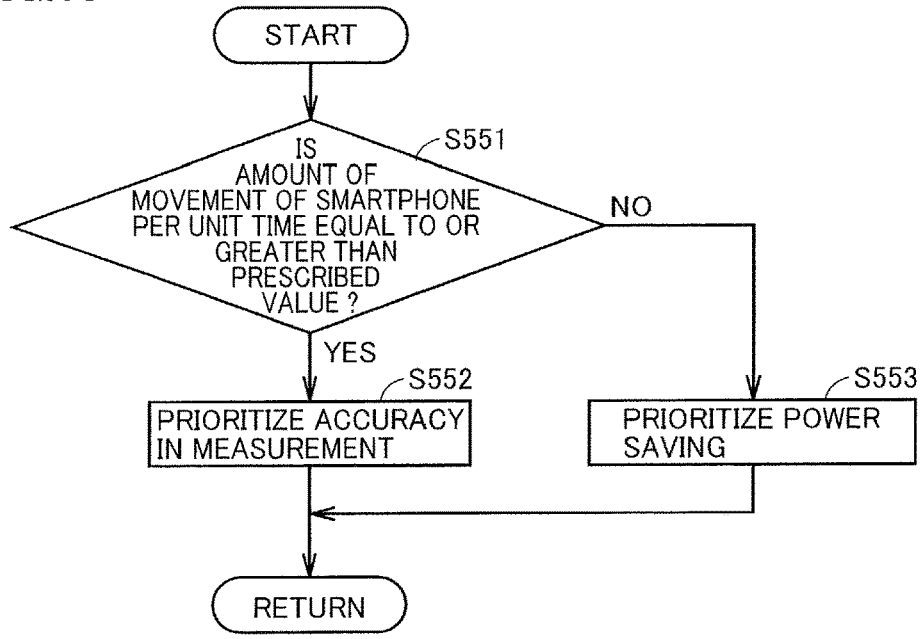
FIG. 19 is a flowchart showing a ninth embodiment of determination of prioritized contents in step S101 in FIG. 9.

FIG. 19 is a flowchart showing the ninth embodiment of determination of prioritized contents in step S101 in FIG. 9.

When movement amount detection unit 5 detects an amount of movement of smartphone 1 per unit time being equal to or greater than a prescribed value in step S551 (S551: YES), the process proceeds to step S552. When movement amount detection unit 5 detects an amount of movement of smartphone 1 per unit time being smaller than the prescribed value (S551: NO), the process proceeds to step S553.

In step S552, transmission control unit 11 can prioritize accuracy in measurement.

In step S553, transmission control unit 11 can prioritize power saving.

[Tenth Embodiment]

In a tenth embodiment, when a result of measurement of pulses of a user in the past indicates fast pulses, pulses are also expected to be fast in measurement conducted from now. Therefore, transmission control unit 11 can prioritize accuracy in measurement.

Figure 20:
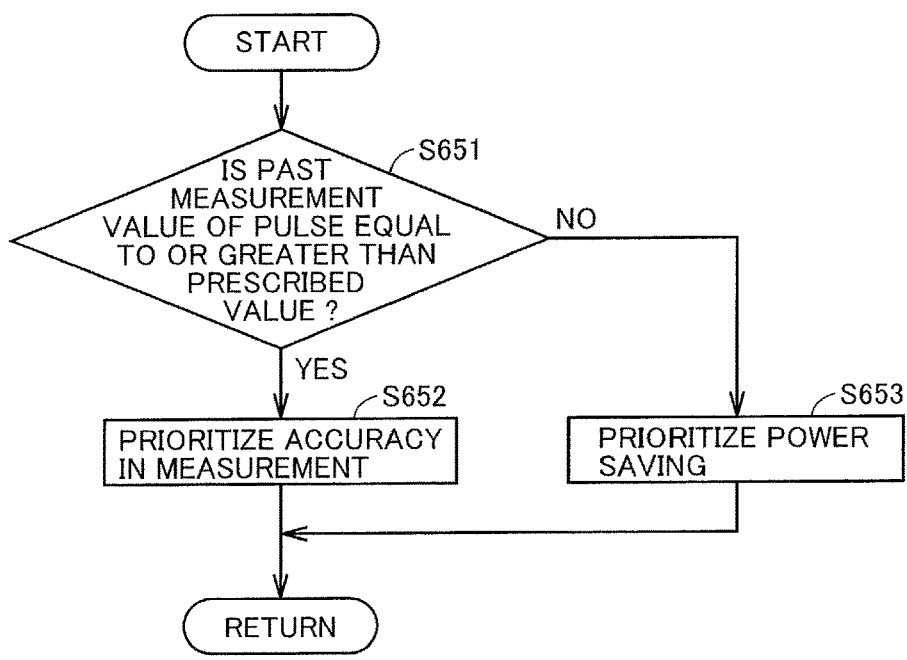
FIG. 20 is a flowchart showing a tenth embodiment of determination of prioritized contents in step S101 in FIG. 9.

FIG. 20 is a flowchart showing the tenth embodiment of determination of prioritized contents in step S101 in FIG. 9.

When a past measurement value of pulses measured by pulse measurement unit 9 and stored in memory 8 is equal to or greater than a prescribed value in step S651 (S651: YES), the process proceeds to step S652. When a past measurement value of pulses measured by pulse measurement unit 9 and stored in memory 8 is smaller than the prescribed value (S651: NO), the process proceeds to step S653.

In step S652, transmission control unit 11 can prioritize accuracy in measurement.

In step S653, transmission control unit 11 can prioritize power saving.

[Eleventh Embodiment]

In an eleventh embodiment, transmission control unit 11 can switch between contents prioritized until reflected light is first detected after start of measurement of pulses and contents prioritized after that.

Figure 21:
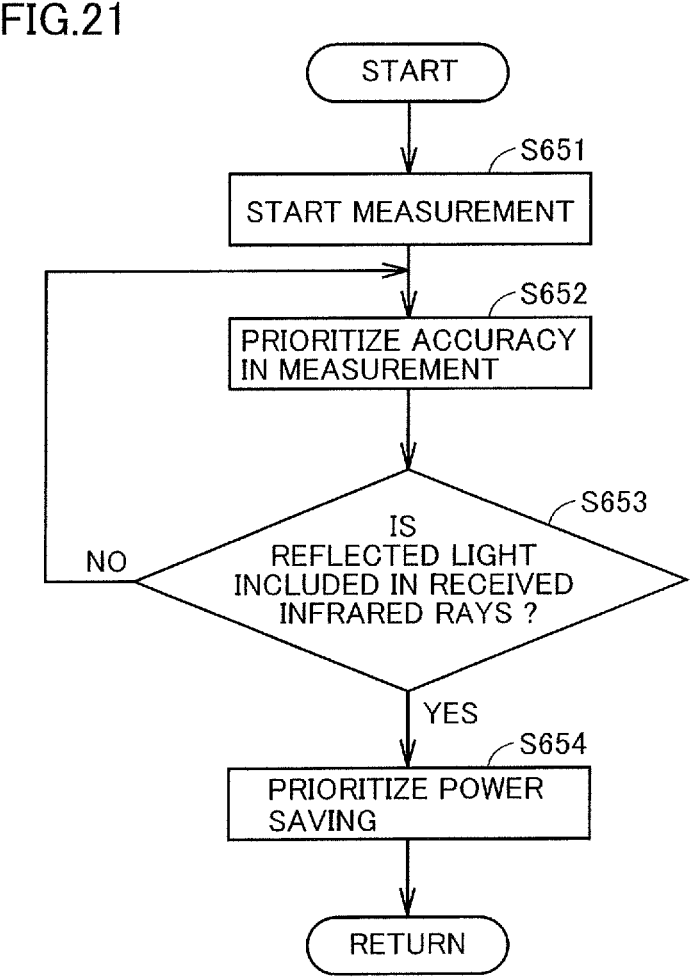
FIG. 21 is a flowchart showing an eleventh embodiment of determination of prioritized contents in step S101 in FIG. 9.

FIG. 21 is a flowchart showing the eleventh embodiment of determination of prioritized contents in step S101 in FIG. 9.

In step S651, pulse measurement unit 9 starts measurement.

In step S652, transmission control unit 11 can prioritize accuracy in measurement after start of measurement.

When received infrared rays include reflected light of infrared rays transmitted from infrared transmitter 14 in step S653 (S653: YES), the process proceeds to step S654. When the received infrared rays do not include reflected light (S653: NO), the process returns to step S652.

In step S654, transmission control unit 11 can prioritize power saving.

[Twelfth Embodiment]

In a twelfth embodiment, transmission control unit 11 can vary a pattern of drive of infrared receiver 15 in accordance with a transmission pattern of infrared rays. Specifically, in the twelfth embodiment, an interval of drive of infrared receiver 15 can be varied in accordance with an interval between transmission pulses of infrared rays.

Figure 22:
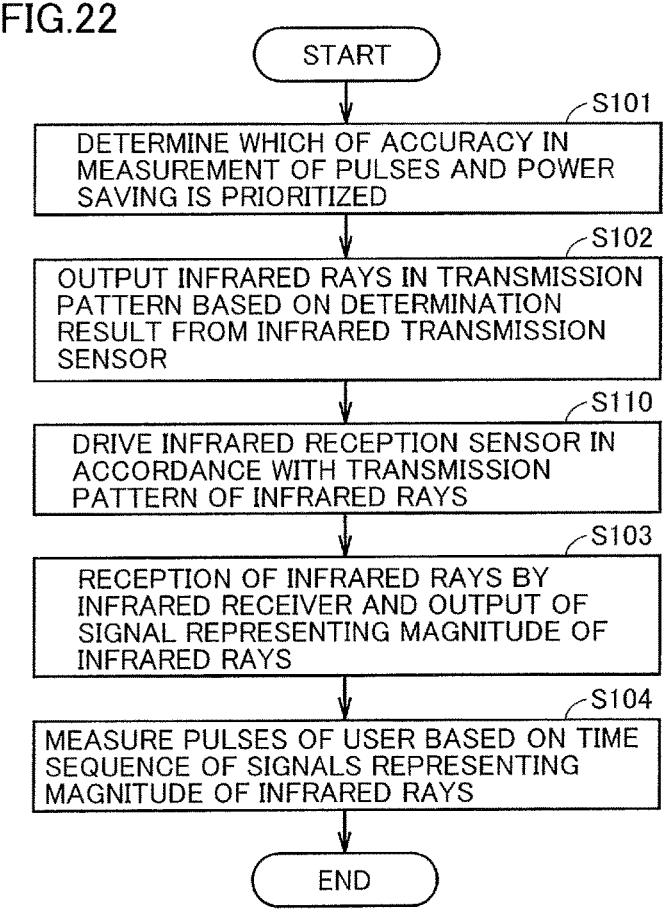
FIG. 22 is a flowchart showing a procedure of measurement of pulses in a twelfth embodiment.

FIG. 22 is a flowchart showing a procedure of measurement of pulses in the twelfth embodiment.

In step S101, transmission control unit 11 can determine which of accuracy in measurement of pulses and power saving is prioritized with the method in any embodiment described previously.

In step S102, transmission control unit 11 can control transmission such that infrared rays in a transmission pattern based on a result of determination are transmitted from infrared transmitter 14.

In step S110, infrared receiver 15 can be driven in accordance with the transmission pattern of infrared rays from infrared transmitter 14.

In step S103, infrared receiver 15 can receive infrared rays and output waveform signals of the received infrared rays.

In step S104, signal reception unit 10 can receive the waveform signals of the infrared rays from infrared receiver 15. Pulse measurement unit 9 can measure pulses of a user based on the waveform signals of the received infrared rays.

Figure 23:
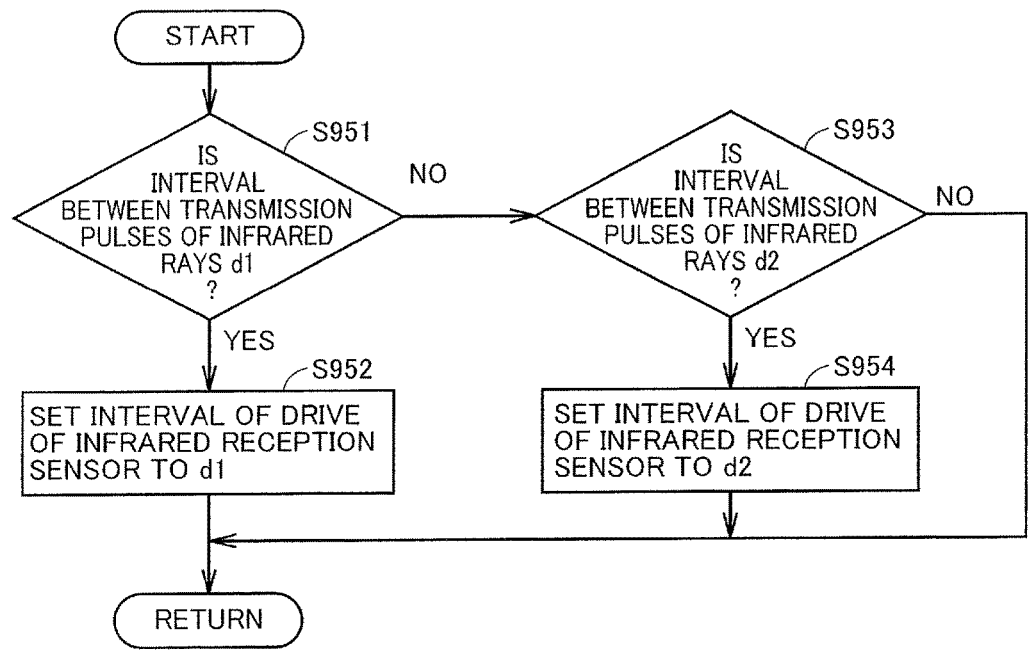
FIG. 23 is a flowchart showing the twelfth embodiment of drive of the infrared receiver in step S110 in FIG. 22.

FIG. 23 is a flowchart showing the twelfth embodiment of drive of infrared receiver 15 in step S110 in FIG. 22.

When an interval between transmission pulses of infrared rays from infrared transmitter 14 is d1 in step S951 (S951: YES), the process proceeds to step S952. When an interval between transmission pulses of infrared rays from infrared transmitter 14 is not d1 (S951: NO), the process proceeds to step S953.

In step S952, reception unit 10 can set an interval of drive of infrared receiver 15 to d1 and output a control signal to infrared receiver 15 in synchronization with the timing of transmission pulses of infrared rays from infrared transmitter 14.

When an interval between transmission pulses of infrared rays from infrared transmitter 14 is d2 in step S953 (S953: YES), the process proceeds to step S954.

In step S954, signal reception unit 10 can set an interval of drive of infrared receiver 15 to d2 and output a control signal to infrared receiver 15 in synchronization with the timing of transmission pulses of infrared rays from infrared transmitter 14.

[Thirteenth Embodiment]

In a thirteenth embodiment, transmission control unit 11 can change power of transmission from infrared transmitter 14 as control of a transmission pattern based on which of accuracy in measurement and power saving is prioritized.

Figure 24:
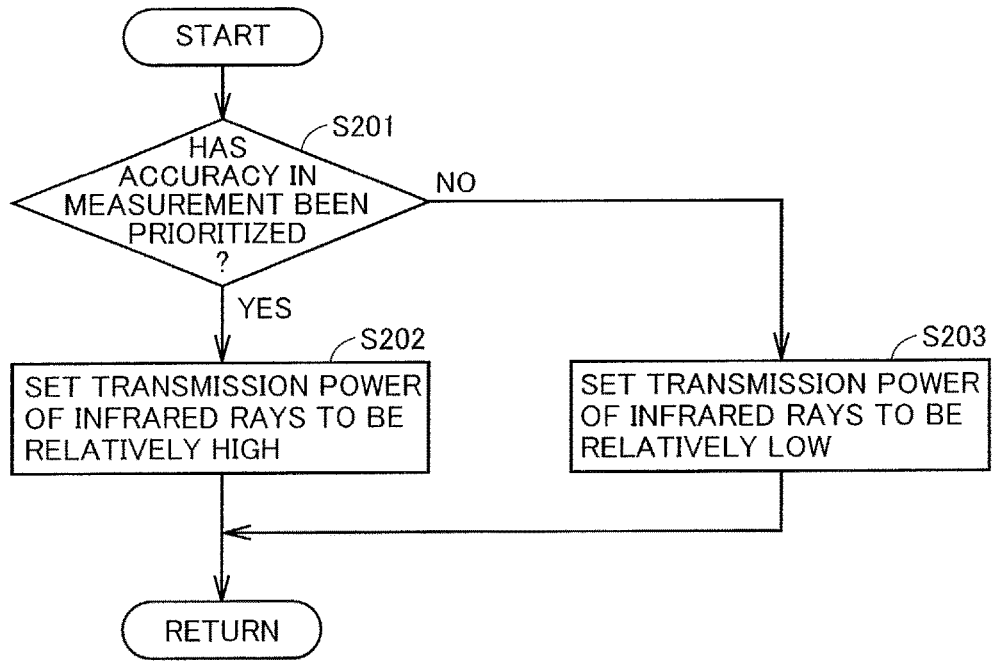
FIG. 24 is a flowchart showing a thirteenth embodiment of control of a transmission pattern in step S102 in FIG. 9.

FIG. 24 is a flowchart showing the thirteenth embodiment of control of a transmission pattern in step S102 in FIG. 9.

When accuracy in measurement has been prioritized in step S201 (S201: YES), the process proceeds to step S202. When power saving has been prioritized (S201: NO), the process proceeds to step S203.

In step S202, transmission control unit 11 can set power of transmission of infrared rays from infrared transmitter 14 to be relatively high.

In step S203, transmission control unit 11 can set power of transmission of infrared rays from infrared transmitter 14 to be relatively low.

Power of transmission of infrared rays in steps S202 and S203 may be designated by a user through input unit 6.

[Fourteenth Embodiment]

In a fourteenth embodiment, transmission control unit 11 can switch between transmission and stop of infrared rays from infrared transmitter 14 as control of a transmission pattern based on which of accuracy in measurement and power saving is prioritized.

Figure 25:
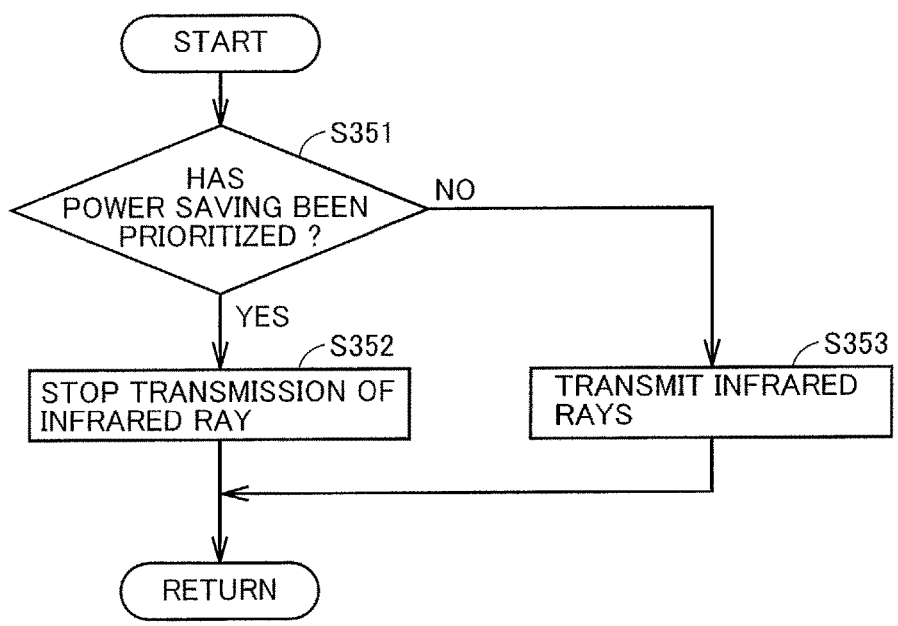
FIG. 25 is a flowchart showing a fourteenth embodiment of control of a transmission pattern in step S102 in FIG. 9.

FIG. 25 is a flowchart showing the fourteenth embodiment of control of a transmission pattern in step S102 in FIG. 9.

When power saving has been prioritized in step S351 (S351: YES), the process proceeds to step S352. When accuracy in measurement has been prioritized (S351: NO), the process proceeds to step S353.

In step S352, transmission control unit 11 can stop transmission of infrared rays from infrared transmitter 14.

In step S353, transmission control unit 11 can allow infrared transmitter 14 to transmit infrared rays.

[Fifteenth Embodiment]

In a fifteenth embodiment, transmission control unit 11 can switch between successive emission and normal emission of transmission pulses from infrared transmitter 14 as control of a transmission pattern based on which of accuracy in measurement and power saving is prioritized.

Figure 26:
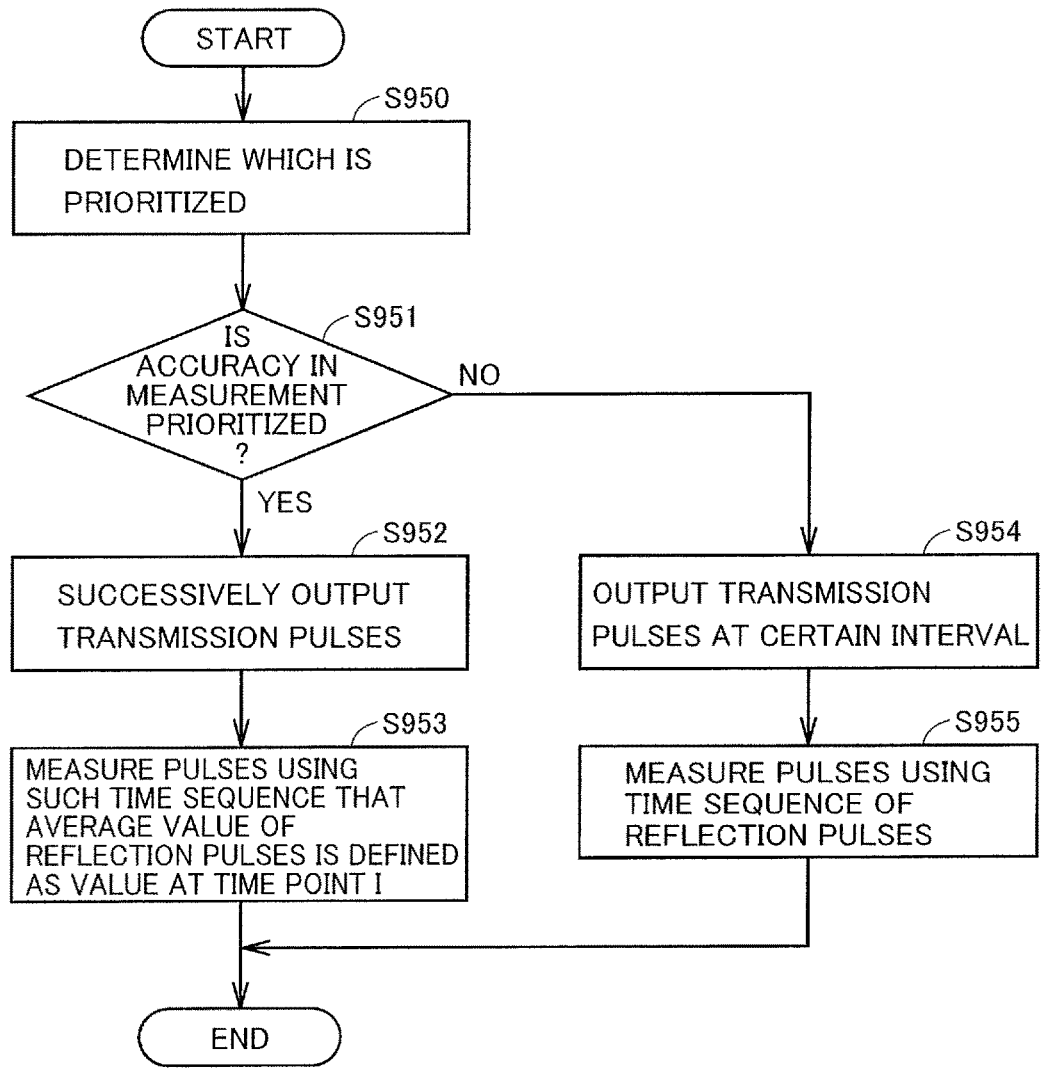
FIG. 26 is a flowchart showing a fifteenth embodiment of control of a transmission pattern in step S102 in FIG. 9.
Figure 27:
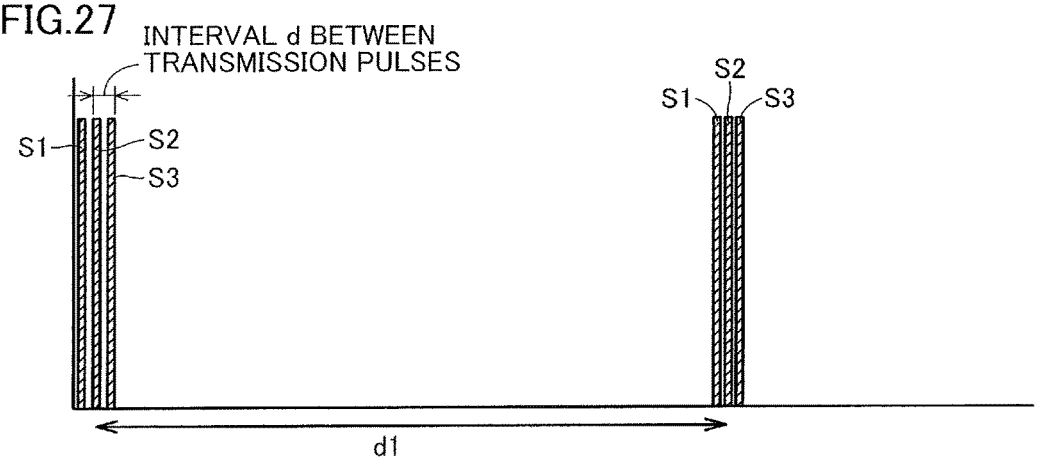
FIG. 27 is a diagram showing an example of transmitted transmission pulses.
Figure 28:
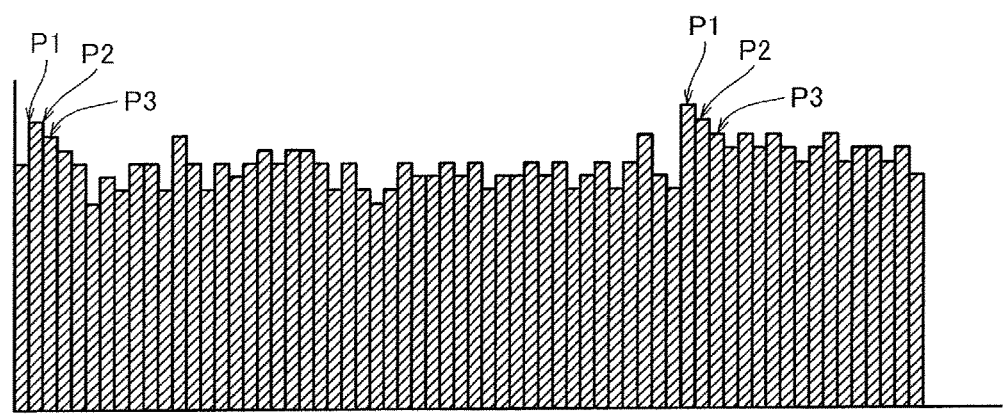
FIG. 28 is a diagram showing an example of reflection pulses.

FIG. 26 is a flowchart showing the fifteenth embodiment of control of a transmission pattern in step S102 in FIG. 9. FIG. 27 is a diagram showing an example of transmitted transmission pulses. FIG. 28 is a diagram showing an example of reflection pulses.

In step S950, transmission control unit 11 can determine which of accuracy in measurement of pulses and power saving is prioritized with the method in any embodiment described previously.

When accuracy in measurement is prioritized in step S951 (S951: YES), the process proceeds to step S952. When power saving is prioritized (S951: NO), the process proceeds to step S953.

In step S952, transmission control unit 11 can control transmission such that a plurality of successive transmission pulses (transmission pulses S1, S2, and S3 in FIG. 27) are transmitted at a certain interval d1 from infrared transmitter 14 as shown in FIG. 27.

In step S953, infrared receiver 15 can receive infrared rays and output waveform signals of received infrared rays. Signal reception unit 10 can receive waveform signals of infrared rays from infrared receiver 15. Pulse measurement unit 9 can measure pulses of a user based on such a time sequence that an average value of magnitude of signals of reflection pulses of the plurality of transmission pulses is defined as a value at one time point. In the example in FIG. 28, an average value of magnitude P1, P2 and P3 of signals of three reflection pulses is defined as a value at one time point. Thus, even when pulses considerably fluctuate, for example, during workout, accuracy in measurement can be prevented from lowering.

In step S954, transmission control unit 11 can control transmission such that one transmission pulse is transmitted from infrared transmitter 14 at certain interval dl.

In step S955, infrared receiver 15 can receive infrared rays and output waveform signals of received infrared rays. Signal reception unit 10 can receive waveform signals of infrared rays from infrared receiver 15. Pulse measurement unit 9 can measure pulses of a user based on such a time sequence that a signal of each reflection pulse is defined as a value at one time point.

[Sixteenth Embodiment]

In a sixteenth embodiment, when received light includes reflected light and also much noise resulting from external light, it is highly likely that a user is not properly wearing earphone 51 in an ear and accuracy in measurement is expected to become lower in such a condition. Therefore, smartphone 1 can give a notification to the user. This notification is given by audio output through dynamic speaker 17 of earphone 51 and through representation of a message through display 7.

When received light consists of noise resulting from external light, it is likely that earphone 51 is not attached to an ear of a user. Therefore, smartphone 1 can give a notification to the user. Since the user is not wearing earphone 51, the notification can be given not by audio output but by representation of a message through display 7.

Furthermore, when an application for workout has been launched, the user desires measurement of pulses. Therefore, smartphone 1 can give the notification described above. When the application for workout has not been launched, the user does not desire measurement of pulses, and hence the notification described above is not given.

FIG. 29 is a flowchart showing a procedure of processing for notification in the sixteenth embodiment.

When received infrared rays include reflected light of infrared rays transmitted from infrared transmitter 14 in step S151 (S151: YES), the process proceeds to step S152. When the received infrared rays do not include reflected light (S151: NO), the process proceeds to step S156.

In step S152, transmission control unit 11 can prioritize accuracy in measurement.

When received infrared rays include a prescribed amount or more of noise component in step S153 (S153: YES), the process proceeds to step S154.

When an application for work application has been launched in step S154 (S154: YES), the process proceeds to step S155.

In step S155, transmission control unit 11 can instruct audio output unit 12 to output voice and sound indicating that the earphone has not properly been attached to the ear through dynamic speaker 17 of earphone 51 and can have display 7 show a message indicating that the earphone has not properly been attached to the ear.

In step S156, transmission control unit 11 can prioritize power saving.

When an application for work application has been launched in step S157 (S157: YES), the process proceeds to step S158.

In step S158, transmission control unit 11 can have display 7 show a message indicating that the earphone has not been attached to the ear.

When determination as NO is made in step S153, S154, or S157, the process ends.

In a modification of the sixteenth embodiment, when determination as YES is made in S153 and determination as YES is made in S157 regardless of whether or not an application for workout has been launched, the process may proceed to step S155 and step S158, respectively.

(Modification)

The present disclosure is not limited to embodiments above and includes a modification, for example, as below.

(1) An embodiment above is not necessarily executable alone but embodiments can be combined.

(2) Visible Light

In embodiments, though smartphone 1 uses infrared rays as one example of light used for measurement of pulses, limitation thereto is not intended. For example, smartphone 1 can measure pulses with a similar method also with the use of visible light (green light).

(3) Electronic Device

Though a smartphone is described by way of example of an electronic device in embodiments, the electronic device in the present disclosure is not limited to the smartphone but devices such as portable terminals, personal computers, or tablets of other types are also encompassed.

It should be understood that embodiments disclosed herein are illustrative and non-restrictive in every respect. The scope of the present disclosure is defined by the terms of the claims rather than the description above and is intended to include any modifications within the scope and meaning equivalent to the terms of the claims.

The invention claimed is:

1. An electronic device configured to control an earphone which includes an infrared transmitter and an infrared receiver, the electronic device comprising:
   at least one processor configured to control transmission of infrared rays from the infrared transmitter; and
   a reception unit configured to receive waveform signals of the infrared rays received by the infrared receiver,
   the at least one processor being configured to measure pulses of a user who wears the earphone based on the waveform signals and to control a transmission pattern of the infrared rays from the infrared transmitter based on which of accuracy in measurement of the pulses and power saving is prioritized, wherein accuracy in measurement is prioritized when the earphone is not properly attached to the user's ear as indicated by the received infrared rays including external light.

2. The electronic device according to claim 1, wherein the at least one processor is configured to increase transmission power of the infrared rays when the accuracy in measurement is prioritized and to decrease transmission power of the infrared rays when the power saving is prioritized.

3. The electronic device according to claim 1, wherein the at least one processor is configured to make an interval between transmission pulses of the infrared rays shorter when the accuracy in measurement is prioritized and to make an interval between transmission pulses of the infrared rays longer when the power saving is prioritized.

4. The electronic device according to claim 1, wherein the at least one processor is configured to stop transmission of the infrared rays when the power saving is prioritized.

5. The electronic device according to claim 1, wherein the at least one processor is configured to successively transmit transmission pulses of the infrared rays when the accuracy in measurement is prioritized and to measure the pulses by using an average value of reflection pulses corresponding to the respective transmission pulses of the infrared rays.

6. The electronic device according to claim 1, wherein the at least one processor is configured to prioritize the accuracy in measurement when attachment of the earphone to an ear is confirmed or when probability of attachment of the earphone to the ear is determined as relatively high and to prioritize the power saving when probability of attachment of the earphone to the ear is determined as relatively low.

7. The electronic device according to claim 6, wherein the at least one processor is configured to prioritize the accuracy in measurement when reflected light of the infrared rays transmitted from the infrared transmitter is included in the received infrared rays.

8. The electronic device according to claim 6, wherein the at least one processor is configured to prioritize the accuracy in measurement during a certain period immediately after connection of the earphone to the electronic device as compared with a period outside the certain period.

9. The electronic device according to claim 6, wherein
the at least one processor is configured to prioritize the power saving when a certain period of time has elapsed without detection of attachment of the earphone to the ear after connection of the earphone to the electronic device.

10. The electronic device according to claim 6, wherein
the at least one processor is configured to operate an application, and
the at least one processor is configured to prioritize the accuracy in measurement during a certain period immediately after launch of a specific application with the earphone being connected to the electronic device, as compared with a period outside the certain period.

11. The electronic device according to claim 6, the electronic device comprising a detection unit configured to detect movement or stop of the electronic device, wherein
the at least one processor is configured to prioritize the power saving during a period in which the earphone is connected to the electronic device and the electronic device is detected to be in a rest state, as compared with a period outside the period.

12. The electronic device according to claim 1, wherein
the at least one processor is configured to prioritize the accuracy in measurement from immediately after start of measurement until detection that the received infrared rays include reflected light of the infrared rays transmitted from the infrared transmitter and configured to prioritize the power saving after detection.

13. The electronic device according to claim 1, wherein
the at least one processor is configured to prioritize the accuracy in measurement when the pulses are expected to be equal to or greater than a prescribed value as compared with when the pulses are expected to be smaller than the prescribed value.

14. The electronic device according to claim 1, the electronic device comprising a detection unit configured to detect an amount of movement of the electronic device per unit time, wherein
the at least one processor is configured to prioritize the accuracy in measurement when an amount of movement of the electronic device per unit time is equal to or greater than a prescribed value.

15. The electronic device according to claim 1, the electronic device comprising a storage unit configured to store a measurement value of the pulses, wherein
the at least one processor is configured to prioritize the accuracy in measurement when a past measurement value of pulses which is stored in the storage unit is equal to or greater than a prescribed value.

16. The electronic device according to claim 1, wherein
the at least one processor is configured to prioritize the power saving during a period in which the earphone is connected to the electronic device and the electronic device is in a power saving mode, as compared with a period outside the period.

17. The electronic device according to claim 1, wherein
the reception unit is configured to control drive of the infrared receiver in accordance with the transmission pattern of the infrared rays.

18. The electronic device according to claim 1, wherein
the at least one processor is configured to notify that the earphone is not attached to an ear when the received infrared rays do not include reflected light of the infrared rays transmitted from the infrared transmitter.

19. The electronic device according to claim 1, wherein
the at least one processor is configured to notify that the earphone is not properly attached to an ear when the received infrared rays include the external light.

20. An electronic device configured to control an earphone including an optical transmitter and an optical receiver, the electronic device comprising:
at least one processor configured to control transmission of light from the optical transmitter; and
a reception unit configured to receive a waveform signal of light received by the opticaleceiver; and
a detection unit configured to detect movement of the electronic device,
the at least one processor being configured to measure pulses of a user who wears the earphone based on a waveform signal of the received light and to control a transmission pattern of light from the optical transmitter based on which of accuracy in measurement of the pulses and power saving is prioritized, and wherein the at least one processor is further configured to prioritize the power saving during a period in which the earphone is connected to the electronic device and the electronic device is detected to be in a rest state.

* * * * *